May 12, 1959 E. S. BOERNER Plant Pat. 1,833
ROSE PLANT
Filed Oct. 22, 1958
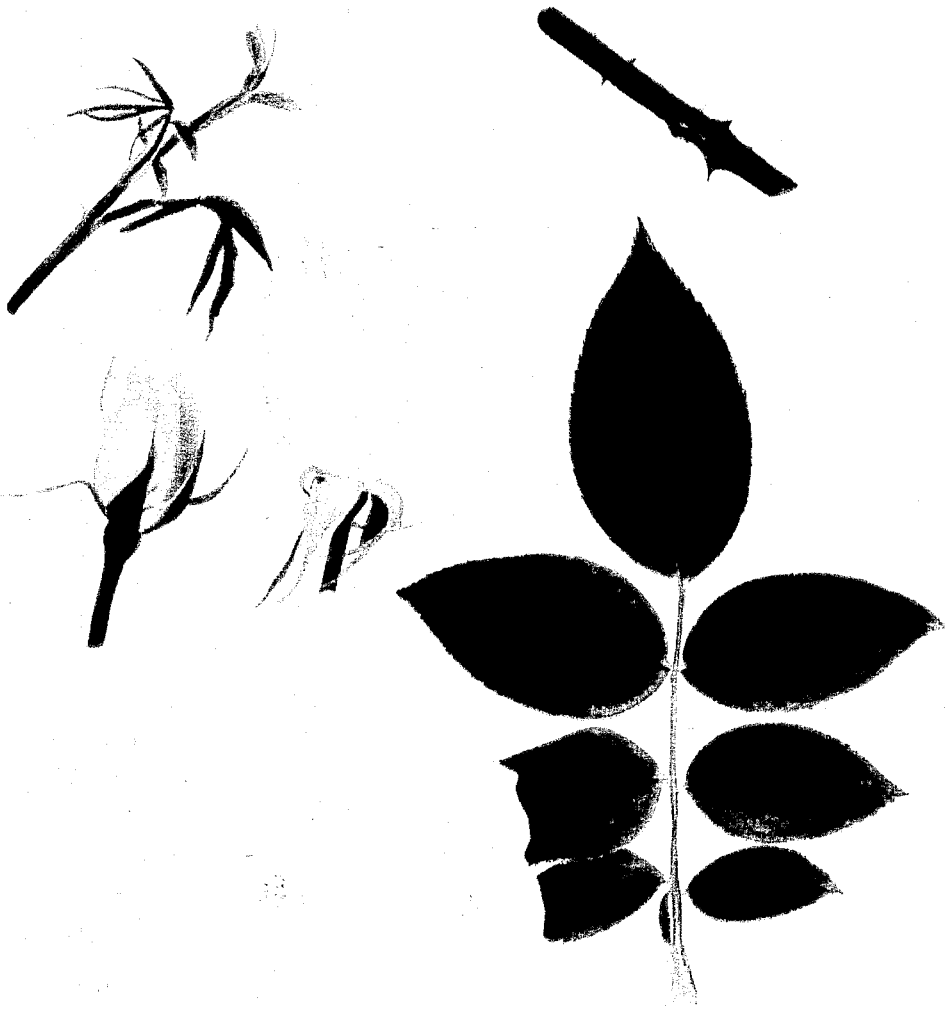
Inventor.
E. S. Boerner
By: Robb & Robb
Attorneys United States Patent Office Plant Pat. 1,833
Patented May 12, 1959

1,833

ROSE PLANT

Eugene S. Boerner, Newark, N.Y., assignor to Jackson & Perkins Company, Newark, N.Y., a corporation of New York Application October 22, 1958, Serial No. 769,050

1 Claim. (Cl. 47—61)

The present invention relates to a new and distinct variety of rose plant of the hybrid tea class, which was originated by me by crossing the variety "Golden Masterpiece" (Plant Patent No. 1,284) with an unnamed and unpatented hybrid tea seedling that is characterized by its coral colored flowers.

The general objective of this breeding was a part of a broader objective to produce a rose variety having the floriferousness of the parent variety "Golden Masterpiece" and a larger flower size, but having flowers of colors different from the normal color of "Golden Masterpiece." The present variety is the result of the achievement of one of the new color phases of the general objective, and in addition thereto, other desirable improvements have been attained. The new variety is definitely differentiated from its parents, as well as from all other varieties of which I am aware, as evidenced by the unique combination of characteristics amongst which the following are outstanding:

(1) A free-growing plant habit;

(2) Distinctive foliage composed of long and oval pointed leaflets;

(3) Very large hybrid tea type blooms ranging from 6 inches to 6½ inches in diameter when fully expanded;

(4) A distinctive and brilliant Geranium Pink general color tonality of the flowers, with the outer edges of the flower petals shading to Begonia Rose, and the constancy of this coloration throughout the life of the flower, said coloration being very new in roses of the hybrid tea class; and (5) A delightful flower fragrance which is very firm and lasting.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.

*Seed parent.*—"Golden Masterpiece."

*Pollen parent.*—An unnamed hybrid tea seedling having coral-colored flowers.

Classification:

*Botanic.*—Hybrid tea.

*Commercial.*—Hybrid tea.

*Flower*

(Observations made from specimens grown in a greenhouse at Newark, New York, near mid-afternoon in the latter part of June.)

Blooming habit: Recurrent—continuous.

Bud:

*Size.*—Very large.

*Form.*—Long; pointed; is not affected by wet or hot weather.

*Color.*—When sepals first divide—Carmine, Plate 1. When petals begin to unfurl—Spectrum Red. Plate 1. When half-blown: inside of petals—Rose Doree, Plate 1; reverse of petals—Begonia Rose, Plate 1.

*Sepals.*—Slightly branched; curl back when petals begin to unfurl. Color: inside—Pale Fluorite Green, Plate 32; outside—Light Bice Green, Plate 17.

*Calyx.*—Color—Bice Green, Plate 17. Shape—pear. Size—broad. Aspect—smooth. Odor when rubbed—none.

*Peduncle.* — Length — long. Aspect — smooth. Strength—erect; heavy. Color—Biscay Green, Plate 17.

*Opening.*—Opens up well; is not affected by adverse weather conditions.

Bloom:

*Size.*—Very large. Average size when fully expanded—from 6 inches to 6½ inches.

*Borne.*—Both singly and several together.

*Stems.*—Long; strong.

*Form (when first open).*—High-centered. Permanence—retains its form to the end.

*Petalage.*—Double (full but open center). Number of petals under normal conditions—from 30 to 35.

*Color.* — Center of flower — Rose Doree, Plate 1. Outer petals—Geranium Pink, Plate 1, lightly overcast with Eosine Pink, Plate 1. Base of petals (aiglet) — Amber Yellow, Plate 16. Inside of petals—Geranium Pink, Plate 1, with outer edges of petal Begonia Rose, Plate 1. Reverse of petals—Eosine Pink, Plate 1, with outer edges of petal Begonia Rose, Plate 1.

*General tonality from a distance.*—Geranium Pink, Plate 1, with edges of petals Begonia Rose, Plate 1.

*Discoloration.*—General tonality at end of first day—Rose Doree, Plate 1. Second day — Geranium Pink, Plate 1, with outer edges of petals Begonia Rose, Plate 1. Third day—Geranium Pink, Plate 1, with outer edges of petals lightly overcast with Begonia Rose, Plate 1.

Petals:

*Texture.*—Thick; leathery; is not affected by wet or hot weather.

*Appearance.*—Inside—satiny. Outside—shiny.

*Form.*—Oval.

*Arrangement.* — Imbricated (regularly arranged shingle-like).

*Petaloids in center.*—Few; large.

*Persistence.*—Drop off cleanly.

*Fragrance.*—Strong. Nature—tea (average hybrid tea scent).

*Lasting quality.* — On the plant — long. As cut flower—long.

*Genital organs*

Stamens, anthers: Medium size; many; regularly arranged around styles. Color—Capucine Yellow, Plate 3.

Stamens, filaments (threads): Medium length. Color—Eosine Pink, Plate 1.

Pollen: Color—Pale Yellow-Orange, Plate 3.

Styles: Bunched; uneven length; medium length; thin.

Stigmas: Color—Cream Color, Plate 16.

Ovaries: All enclosed in calyx.
Hips: None.
Seeds: None.

*Plant*

Form: Bush.
Growth: Very vigorous; upright.
Foliage: Compound of 5–7 leaflets.
*Size.*—Large.
*Quantity.*—Normal.
*Color.*—New foliage: upper side—Parrott Green, Plate 6, with edges of leaf lightly overcast with Garnet Brown, Plate 1; under side — Madder Brown, Plate 8. Old foliage: Upper side—Deep Dull Yellow-Green, Plate 32; under side—Light Bice Green, Plate 17.
*Shape.*—Long oval pointed.
*Texture.* — Upper side — leathery. Under side — smooth.
*Ribs and veins.*—Ordinary.
*Edge.*—Serrated (saw-toothed).
*Serration.*—Both double and single; small.
*Leaf stem.*—Color—Biscay Green, Plate 17. Under side—prickly.
*Stipules.*—Medium length; smooth.
Wood:
*New wood.*—Color—Oil Green, Plate 5. Bark—smooth.

*Old wood.* — Color — Varley's Green, Plate 18. Bark—smooth.
Thorns:
*Thorns.*—Quantity: on main stalks from base—many; on laterals from stalk—many. Form—Narrow base; medium length; hooked downward. Color (when young)—Acajou Red, Plate 13. Position—irregular.
*Prickles.*—Quantity: on main stalks—none; on laterals—none.
*Short needles.*—Quantity: on main stalks—none; on laterals—none.

I claim:

A new and distinct variety of rose plant of the hybrid tea class, substantially as herein shown and described, characterized particularly as to novelty by the unique combination of a free-growing plant habit, distinctive foliage composed of long and oval pointed leaflets, very large blooms, a distinctive and brilliant Geranium Pink general color tonality of the flowers with Begonia Rose on the outer edges of the flower petals, said coloration being relatively constant throughout the life of the flower, and a good flower fragrance which is very firm and lasting.

No references cited.